US008068890B2

(12) United States Patent
Boyce et al.

(10) Patent No.: US 8,068,890 B2
(45) Date of Patent: Nov. 29, 2011

(54) PULSE OXIMETRY SENSOR SWITCHOVER

(75) Inventors: Robin S. Boyce, Pleasanton, CA (US); Brad Nordstrom, Alameda, CA (US); Arie Ravid, Fremont, CA (US); Hui Wang, San Ramon, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1461 days.

(21) Appl. No.: 11/540,248

(22) Filed: Sep. 29, 2006

(65) Prior Publication Data

US 2008/0081970 A1    Apr. 3, 2008

(51) Int. Cl.
*A61B 5/1455* (2006.01)

(52) U.S. Cl. .......................................... 600/323; 600/310

(58) Field of Classification Search ........... 600/309–344
See application file for complete search history.

(56) References Cited

U.S. PATENT DOCUMENTS

| | | | |
|---|---|---|---|
| 3,638,640 A | 2/1972 | Shaw | |
| 4,714,341 A | 12/1987 | Hamaguri et al. | |
| 4,800,885 A * | 1/1989 | Johnson | 600/330 |
| 4,805,623 A | 2/1989 | Jöbsis | |
| 4,807,631 A | 2/1989 | Hersh et al. | |
| 4,819,646 A * | 4/1989 | Cheung et al. | 600/323 |
| 4,846,183 A * | 7/1989 | Martin | 600/336 |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,119,815 A | 6/1992 | Chance | |
| 5,122,974 A | 6/1992 | Chance | |
| 5,167,230 A | 12/1992 | Chance | |
| 5,190,038 A * | 3/1993 | Polson et al. | 600/330 |
| 5,246,003 A | 9/1993 | DeLonzor | |
| 5,247,931 A | 9/1993 | Norwood | |
| 5,263,244 A | 11/1993 | Centa et al. | |
| 5,275,159 A | 1/1994 | Griebel | |

(Continued)

FOREIGN PATENT DOCUMENTS

DE   102 13 692 A1   10/2003

(Continued)

OTHER PUBLICATIONS

Lee, Jason C.S., et al., "Measurement of Percent Carboxyhemoglobin with Pulse-Oximetry Technique," *IEEE Engineering in Medicine & Biology Society 10th Annual International Conference*, CH2566-88, vol. 88, pp. 1781-1782 (1988).

(Continued)

*Primary Examiner* — Eric Winakur
*Assistant Examiner* — Marjan Fardanesh

(57) ABSTRACT

Switchover of a filtered and unfiltered pulse oximetry sensor is provided with gain controlled amplifiers controlled by separate gain control voltages that may change in opposite directions over a period of time. The outputs of the gain controlled amplifiers may be coupled to voltage-to-current converters whose outputs may be coupled in parallel. The parallel coupled outputs of the voltage-to-current converters may produce a current signal representative of the output of the gain controlled amplifier having the highest gain/signal.

21 Claims, 2 Drawing Sheets

U.S. PATENT DOCUMENTS

| | | |
|---|---|---|
| 5,279,295 A | 1/1994 | Martens et al. |
| 5,297,548 A | 3/1994 | Pologe |
| 5,348,004 A * | 9/1994 | Hollub .................. 600/323 |
| 5,355,880 A | 10/1994 | Thomas et al. |
| 5,372,136 A | 12/1994 | Steuer et al. |
| 5,385,143 A | 1/1995 | Aoyagi |
| 5,390,670 A | 2/1995 | Centa et al. |
| 5,413,099 A | 5/1995 | Schmidt et al. |
| 5,469,845 A | 11/1995 | DeLonzor et al. |
| 5,482,036 A | 1/1996 | Diab et al. |
| 5,483,646 A | 1/1996 | Uchikoga |
| 5,553,614 A | 9/1996 | Chance |
| 5,564,417 A | 10/1996 | Chance |
| 5,575,285 A | 11/1996 | Takanashi et al. |
| 5,611,337 A | 3/1997 | Bukta |
| 5,630,413 A | 5/1997 | Thomas et al. |
| 5,645,059 A | 7/1997 | Fein et al. |
| 5,645,060 A | 7/1997 | Yorkey |
| 5,680,857 A | 10/1997 | Pelikan et al. |
| 5,692,503 A | 12/1997 | Keunstner |
| 5,730,124 A | 3/1998 | Yamauchi |
| 5,758,644 A | 6/1998 | Diab et al. |
| 5,779,631 A | 7/1998 | Chance |
| 5,782,757 A | 7/1998 | Diab et al. |
| 5,786,592 A | 7/1998 | Hök |
| 5,830,136 A | 11/1998 | DeLonzor et al. |
| 5,830,139 A | 11/1998 | Abreu |
| 5,842,981 A | 12/1998 | Larsen et al. |
| 5,871,442 A | 2/1999 | Madarasz et al. |
| 5,873,821 A | 2/1999 | Chance et al. |
| 5,995,856 A | 11/1999 | Mannheimer et al. |
| 6,011,986 A | 1/2000 | Diab et al. |
| 6,064,898 A | 5/2000 | Aldrich |
| 6,081,742 A | 6/2000 | Amano et al. |
| 6,088,607 A | 7/2000 | Diab et al. |
| 6,120,460 A | 9/2000 | Abreu |
| 6,134,460 A | 10/2000 | Chance |
| 6,150,951 A | 11/2000 | Olejniczak |
| 6,154,667 A | 11/2000 | Miura et al. |
| 6,163,715 A | 12/2000 | Larsen et al. |
| 6,181,958 B1 | 1/2001 | Steuer et al. |
| 6,181,959 B1 | 1/2001 | Schöllermann et al. |
| 6,230,035 B1 | 5/2001 | Aoyagi et al. |
| 6,266,546 B1 | 7/2001 | Steuer et al. |
| 6,285,895 B1 | 9/2001 | Ristolainen et al. |
| 6,312,393 B1 | 11/2001 | Abreu |
| 6,353,750 B1 | 3/2002 | Kimura et al. |
| 6,397,091 B2 | 5/2002 | Diab et al. |
| 6,415,236 B2 | 7/2002 | Kobayashi et al. |
| 6,419,671 B1 | 7/2002 | Lemberg |
| 6,438,399 B1 | 8/2002 | Kurth |
| 6,461,305 B1 | 10/2002 | Schnall |
| 6,466,809 B1 | 10/2002 | Riley |
| 6,487,439 B1 | 11/2002 | Skladnev et al. |
| 6,501,974 B2 | 12/2002 | Huiku |
| 6,501,975 B2 | 12/2002 | Diab et al. |
| 6,526,301 B2 | 2/2003 | Larsen et al. |
| 6,544,193 B2 | 4/2003 | Abreu |
| 6,546,267 B1 | 4/2003 | Sugiura et al. |
| 6,549,795 B1 | 4/2003 | Chance |
| 6,580,086 B1 | 6/2003 | Schulz et al. |
| 6,591,122 B2 | 7/2003 | Schmitt |
| 6,594,513 B1 | 7/2003 | Jobsis et al. |
| 6,606,509 B2 | 8/2003 | Schmitt |
| 6,615,064 B1 | 9/2003 | Aldrich |
| 6,622,095 B2 | 9/2003 | Kobayashi et al. |
| 6,654,621 B2 | 11/2003 | Palatnik et al. |
| 6,658,277 B2 | 12/2003 | Wasserman |
| 6,662,030 B2 | 12/2003 | Khalil et al. |
| 6,671,526 B1 | 12/2003 | Aoyagi et al. |
| 6,671,528 B2 | 12/2003 | Steuer et al. |
| 6,678,543 B2 | 1/2004 | Diab et al. |
| 6,690,958 B1 | 2/2004 | Walker et al. |
| 6,708,048 B1 | 3/2004 | Chance |
| 6,711,424 B1 | 3/2004 | Fine et al. |
| 6,711,425 B1 | 3/2004 | Reuss |
| 6,785,568 B2 | 8/2004 | Chance |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,829,496 B2 | 12/2004 | Nagai et al. |
| 6,873,865 B2 | 3/2005 | Steuer et al. |
| 6,889,153 B2 | 5/2005 | Dietiker |
| 6,896,661 B2 | 5/2005 | Dekker et al. |
| 6,939,307 B1 | 9/2005 | Dunlop |
| 6,949,081 B1 | 9/2005 | Chance |
| 6,961,598 B2 | 11/2005 | Diab |
| 6,983,178 B2 | 1/2006 | Fine et al. |
| 6,996,427 B2 | 2/2006 | Ali et al. |
| 7,001,337 B2 | 2/2006 | Dekker et al. |
| 7,024,233 B2 | 4/2006 | Ali et al. |
| 7,024,235 B2 | 4/2006 | Melker et al. |
| 7,027,849 B2 | 4/2006 | Al-Ali |
| 7,035,697 B1 | 4/2006 | Brown |
| 7,047,056 B2 | 5/2006 | Hannula et al. |
| 7,127,278 B2 | 10/2006 | Melker et al. |
| 7,130,671 B2 | 10/2006 | Baker, Jr. et al. |
| 7,162,288 B2 | 1/2007 | Nordstrom et al. |
| 7,209,775 B2 | 4/2007 | Bae et al. |
| 7,236,811 B2 | 6/2007 | Schmitt |
| 7,263,395 B2 | 8/2007 | Chan et al. |
| 7,267,652 B2 | 9/2007 | Coyle et al. |
| 7,272,426 B2 | 9/2007 | Schmid |
| 7,440,788 B2 | 10/2008 | Jenkins et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0141914 A1 * | 7/2003 | Buchwald et al. ............ 327/248 |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0107065 A1 | 6/2004 | Al-Ali |
| 2004/0127779 A1 | 7/2004 | Steuer et al. |
| 2004/0163648 A1 | 8/2004 | Burton |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0080323 A1 | 4/2005 | Kato |
| 2005/0085735 A1 | 4/2005 | Baker, Jr. et al. |
| 2005/0101850 A1 | 5/2005 | Parker |
| 2005/0105554 A1 | 5/2005 | Kagan et al. |
| 2005/0107676 A1 | 5/2005 | Acosta et al. |
| 2005/0113656 A1 | 5/2005 | Chance |
| 2005/0159646 A1 | 7/2005 | Nordstrom et al. |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0203357 A1 | 9/2005 | Debreczeny et al. |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |

| | | | |
|---|---|---|---|
| 2006/0030763 | A1 | 2/2006 | Mannheimer et al. |
| 2006/0052680 | A1 | 3/2006 | Diab |
| 2006/0058683 | A1 | 3/2006 | Chance |
| 2006/0064024 | A1 | 3/2006 | Schnall |
| 2006/0195025 | A1 | 8/2006 | Ali et al. |
| 2006/0195028 | A1 | 8/2006 | Hannula et al. |
| 2006/0224058 | A1 | 10/2006 | Mannheimer |
| 2006/0247501 | A1 | 11/2006 | Ali |
| 2006/0258921 | A1 | 11/2006 | Addison et al. |
| 2007/0208240 | A1 | 9/2007 | Nordstrom et al. |
| 2008/0082018 | A1 | 4/2008 | Sackner et al. |
| 2008/0287757 | A1 | 11/2008 | Berson et al. |

FOREIGN PATENT DOCUMENTS

| | | |
|---|---|---|
| JP | 2237544 | 9/1990 |
| JP | 3170866 | 7/1991 |
| JP | 4332536 | 11/1992 |
| JP | 5-212016 | 8/1993 |
| JP | 3238813 | 10/1994 |
| JP | 8256996 | 10/1996 |
| JP | 2003194714 | 7/2003 |
| JP | 2003210438 | 7/2003 |
| JP | 2004008572 | 1/2004 |
| JP | 2004113353 | 4/2004 |
| JP | 2004194908 | 7/2004 |
| JP | 2004248819 | 9/2004 |
| JP | 2004290545 | 10/2004 |
| WO | WO 92/20273 | 11/1992 |
| WO | WO9309711 | 5/1993 |
| WO | WO 94/03102 | 2/1994 |
| WO | W09512349 A1 | 5/1995 |
| WO | WO 97/49330 | 12/1997 |
| WO | WO9843071 | 10/1998 |
| WO | WO9932030 | 7/1999 |
| WO | WO0021438 | 4/2000 |
| WO | WO 01/45553 A1 | 6/2001 |
| WO | WO2006100685 A2 | 9/2006 |

OTHER PUBLICATIONS

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093.

Bongard, Frederic S., et al., "Continuous Dual Oximetry in Surgical critical care—Indications and Limitations," *Annals of Surgery*, vol. 216, No. 1, pp. 60-68 (1992).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engin.*

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Kaestle, S.; "Determining Artefact Sensitivity of New Pulse Oximeters in Laboratory Using Signals Obtained from Patient," *Biomedizinische Technik*, vol. 45 (2000).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Johansson, A.; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Huang, J., et al.; "Low Power Motion Tolerant Pulse Oximetry," *Abstracts*, A7, p. S103 (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Cysewska-Sobusaik, Anna; "Metrological Problems With noninvasive Transillumination of Living Tissues," *Proceedings of SPIE*, vol. 4515, pp. 15-24 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Neumann, R., et al.; "Fourier Artifact suppression Technology Provides Reliable $SpO_2$," *Abstracts*, A11, p. S105 (undated).

* cited by examiner

US 8,068,890 B2

PULSE OXIMETRY SENSOR SWITCHOVER

TECHNICAL FIELD

The present disclosure relates generally to pulse oximetry and, more particularly to switching photodetector sensor output filtering in an oximeter.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Pulse oximetry is a non-invasive method of monitoring the percentage of hemoglobin (hereinafter "Hb") that is saturated with oxygen. A pulse oximeter may include of a pheripheral probe linked to a monitor that may be microprocessor controlled. The probe may be placed on a peripheral part of the body such as a digit (e.g., one finger or toe), ear lobe or nose. Within the probe, there are typically two light emitting diodes (LEDs), one in the visible red spectrum (e.g., 660 nm) and the other in the infrared spectrum (e.g., 940 nm). Using a transmission type sensor, these two beams of light pass through tissue to a photodetector. During passage through tissue, some light is absorbed by blood and soft tissue depending on the concentration of Hb. The amount of light absorption at each light wavelength depends on the degree of oxygenation of Hb within the tissue. By calculating the light absorption at the two wavelengths, the microprocessor of the monitor may compute the proportion of oxygenated Hb. A microprocessor of an oximeter may average oxygen saturation values over five to twenty seconds. The pulse rate may also be calculated from the number of LED cycles between successive pulsatile signals and averaged over a similar variable period of time, depending on the particular oximeter. A monitor may display the percentage of oxygen saturated Hb together with an audible signal for each pulse beat, a calculated heart rate, and in some monitors, a graphical display of the blood flow past the probe. User programmable audible alarms may also be provided.

From the proportions of light absorbed at each light wavelength, the microprocessor may calculate an estimation of the patient's $SpO_2$ level. The monitor may then display the oxygen saturation digitally as a percentage and/or audibly as a tone of varying pitch.

Reflection pulse oximetry uses reflected, rather than transmitted, light on a single-sided sensor. It can therefore be used proximally anatomically, e.g., on the forehead or bowel, although it may be difficult to secure. Other than using specific reflection spectra, the principles are generally the same as for transmission oximetry.

Oximeters may be calibrated during manufacture and may automatically check internal circuits when turned on. Oximeters may be accurate in the range of oxygen saturations of about 70% to 100% (+/ –2%), but may be less accurate under 70%. The pitch of the audible pulse signal may fall in reducing values of saturation. The size of the pulse wave (related to flow) may be displayed graphically. Some models automatically increase the gain of the display when the flow decreases, but in these models, the display may prove misleading. The alarms usually respond to a slow or fast pulse rate or an oxygen saturation below 90%. At this level, there may be a marked fall in $PaO_2$ representing serious hypoxia.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

According to a specific example embodiment of this disclosure, an apparatus for switchover of a pulse oximetry sensor may comprise: a pulse oximetry sensor; a first gain controlled amplifier having an input coupled to the pulse oximetry sensor; a digital filter having an analog input coupled to the pulse oximetry sensor; a second gain controlled amplifier having an input coupled to an analog output of the digital filter; a first voltage-to-current converter having a voltage input coupled to an output of the first gain controlled amplifier; a second voltage-to-current converter having a voltage input coupled to an output of the second gain controlled amplifier; the first and second voltage-to-current converters having outputs coupled together to produce a single current output; and a controller having a first gain control output coupled to the first gain controlled amplifier and a second gain control output coupled to the second gain controlled amplifier, wherein the controller may increase the gain of one of the gain controlled amplifiers over a period of time while decreasing the gain of the other gain controlled amplifier over the same period of time, so that the single current output from the first and second voltage-to-current converters represents the output of the gain controlled amplifier having the highest gain.

According to another specific example embodiment of this disclosure, a method of manufacturing a pulse oximeter may comprise providing a first gain controlled amplifier to which a pulse oximetry sensor may be coupled; coupling the pulse oximetry sensor to a digital filter; coupling the digital filter to a second gain controlled amplifier; coupling the first gain controlled amplifier to a first voltage-to-current converter; coupling the second gain controlled amplifier to a second voltage-to-current converter; and coupling the first and second voltage-to-current converter outputs together to produce a current output wherein the gain of one of the gain controlled amplifiers is adapted to increase over a period of time while the gain of the other gain controlled amplifier is adapted to decrease over the same period of time so that the current output from the first and second voltage-to-current converters represents the gain controlled amplifier having the highest gain.

According to yet another specific example embodiment of this disclosure, a pulse oximeter system having a switchover between unfiltered and filtered channels coupled to a pulse oximetry sensor may comprise: a pulse oximetry sensor; an unfiltered channel comprising a first gain controlled amplifier having an input coupled to the pulse oximetry sensor, and a first voltage-to-current converter having a voltage input coupled to an output of the first gain controlled amplifier; a filtered channel comprising a digital filter having an analog input coupled to the pulse oximetry sensor, a second gain controlled amplifier having an input coupled to an analog output of the digital filter, and a second voltage-to-current converter having a voltage input coupled to an output of the second gain controlled amplifier; the first and second voltage-to-current converters having outputs coupled together to produce a single current output; and a controller having a first gain control output coupled to the first gain controlled amplifier and a second gain control output coupled to the second gain controlled amplifier, wherein when the unfiltered channel is selected the controller may increase the gain of the first gain controlled amplifier over a period of time while decreasing the gain of the second gain controlled amplifier over the same period of time so that the single current output from the first and second voltage-to-current converters represents an unfiltered and amplified signal from the pulse oximetry sensor; and when the filtered channel is selected the controller may increase the gain of the second gain controlled amplifier over a period of time while decreasing the gain of the first gain controlled amplifier over the same period of time so that the single current output from the first and second voltage-to-current converters represents a filtered and amplified signal from the pulse oximetry sensor.

BRIEF DESCRIPTION OF THE DRAWINGS

A more complete understanding of the present disclosure may be acquired by referring to the following description taken in conjunction with the accompanying drawings wherein.

Figure 1:
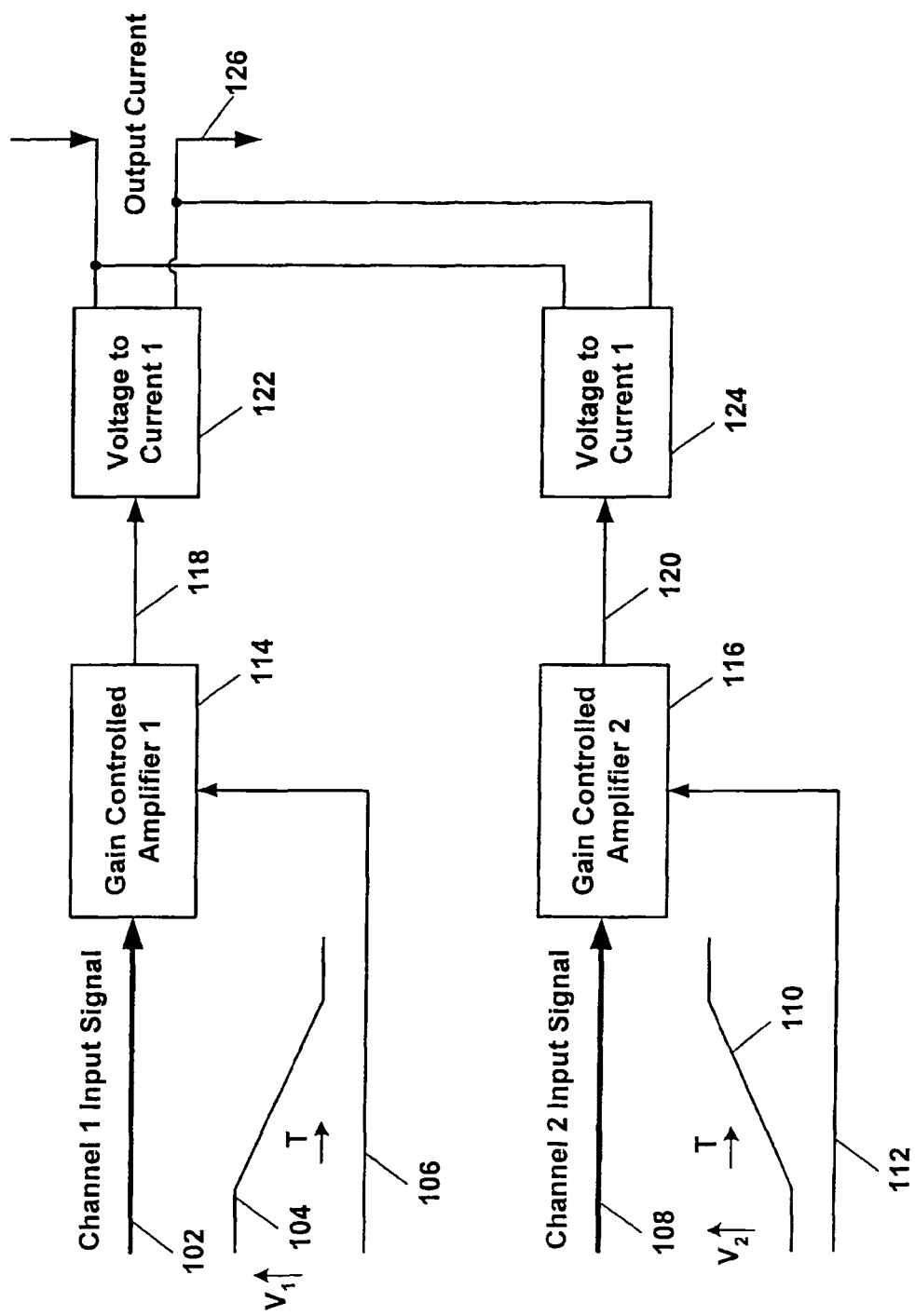
FIG. 1 is a schematic block diagram of a switchover, two channel, gain controlled oximeter sensor amplifier having a current output, according to a specific example embodiment of the present disclosure.

While the present disclosure is susceptible to various modifications and alternative forms, specific example embodiments thereof have been shown in the drawings and are herein described in detail. It should be understood, however, that the description herein of specific example embodiments is not intended to limit the disclosure to the particular forms disclosed herein, but on the contrary, this disclosure is to cover all modifications and equivalents as defined by the appended claims.

DETAILED DESCRIPTION

During testing or use of oximeters, a need exists for an improved method to switch between photodetectors and/or different signal processing paths of a photodetector. Heretofore known switching between photo detectors and/or different signal processing paths of a photodetector has introduced undesirable signal transients that may set off oximeter monitor alarms and/or require longer periods of time for the transient to settle out of the normal five to twenty seconds averaging performed by a microprocessor of an oximeter monitor.

Accordingly, there is a need for improved methods, materials, and/or equipment to switch between photo detectors and/or different signal processing paths of a photo detector, e.g., unfiltered and filtered channels of a pulse oximetry sensor.

Referring now to the drawings, the details of specific example embodiments are schematically illustrated. Like elements in the drawings are represented by like numbers, and similar elements are represented by like numbers with a different lower case letter suffix.

Referring to FIG. 1, depicted is a schematic block diagram of a switchover, two channel, gain controlled oximeter sensor amplifier having a current output, according to a specific example embodiment of the present disclosure. A channel 1 input signal 102 may be applied to a gain controlled amplifier 114, and a channel 2 input signal 108 may be applied to a gain controlled amplifier 116. Gains of the gain controlled amplifiers 114 and 116 may be controlled by gain control signal lines 106 and 112, respectively. The outputs 118 and 120 of the gain controlled amplifiers 114 and 116, respectively, are coupled to voltage-to-current converters 122 and 124, respectively. The current outputs of voltage-to-current converters 122 and 124 may be connected in parallel so as to generate a single switchover output current signal 126. Voltage-to-current converters 122 and 124 may be, for example, but not limited to, optical isolators each having a voltage controlled light emitting diode as an input and a photodetector as an output.

For example, at the beginning of a time period T, gain control signal line 106 has a control voltage 104 at a maximum $V_1$ thereby setting the gain of gain controlled amplifier 114 to a maximum. As the time period T proceeds, control voltage 104 decreases until it is at a minimum $V_1$, thereby reducing the gain of gain controlled amplifier 114. In a similar, but opposite fashion, gain control signal line 112 has a control voltage 110 that starts at the beginning of the time period T at a minimum $V_2$ which may set the gain of gain controlled amplifier 116 to a minimum, and as the time period T proceeds, control voltage 110 increases until it is at a maximum $V_2$, thereby, according to an embodiment, increasing the gain of gain controlled amplifier 116. Output current 126, according to an embodiment, represents the dominate gain controlled amplifier output signal 118 or 120, e.g., the one having the highest gain and signal input will block the other one. Thus, input signal transfer may switch from one of the input channels to the other without introducing a transient in the output current signal 126.

Figure 2:
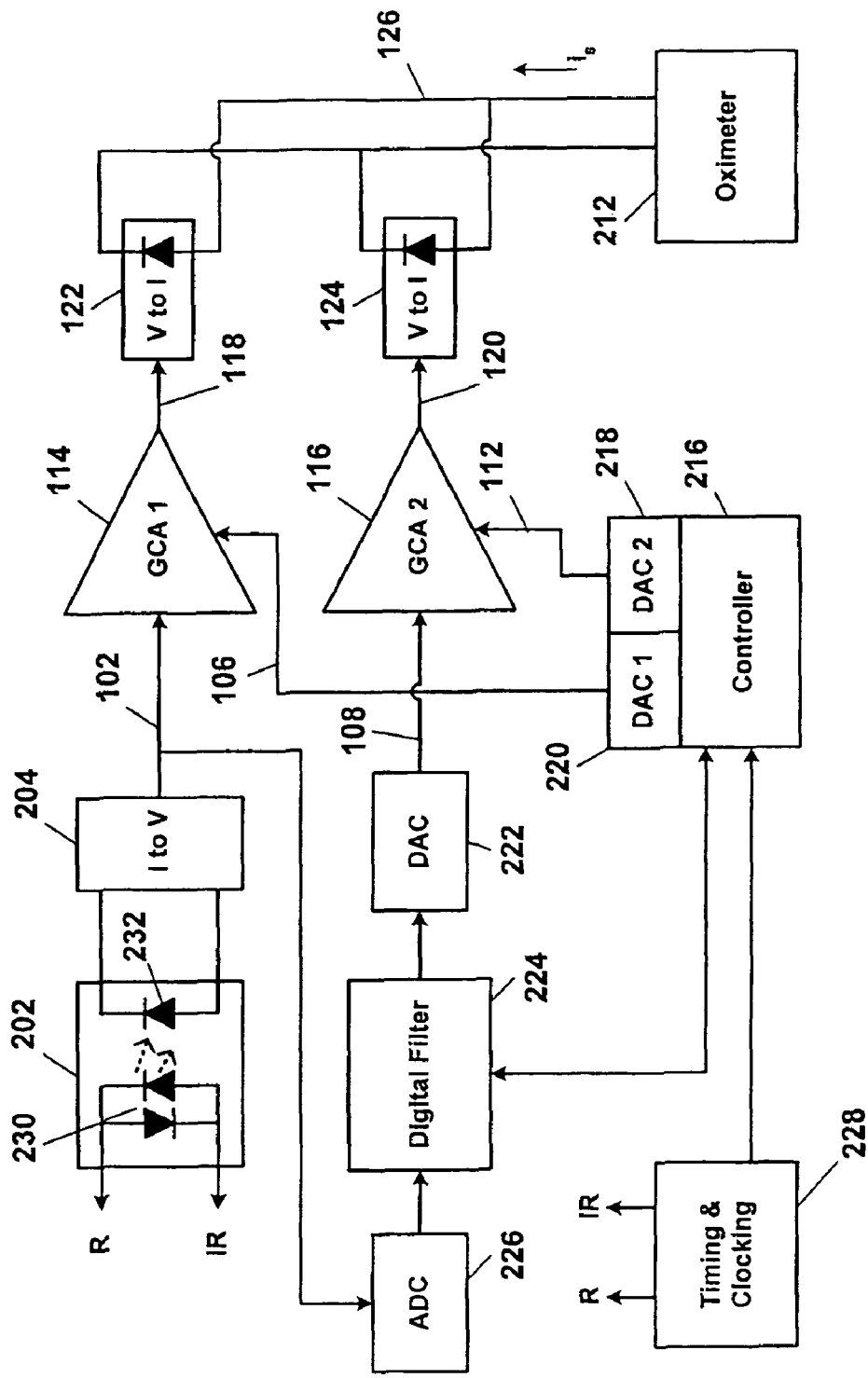
FIG. 2 is a detailed schematic block diagram of a switchover, two channel, gain controlled oximeter sensor amplifier having a current output, according to another specific example embodiment of the present disclosure.

Referring to FIG. 2, depicted is a detailed schematic block diagram of a switchover, two channel, gain controlled oximeter sensor amplifier having a current output, according to another specific example embodiment of the present disclosure. A pulse oximetry peripheral probe 202 may comprise two light emitting diodes (LEDs), one in the visible red spectrum (e.g., 660 nm), and the other in the infrared spectrum (e.g., 940 nm). The sources of light from the two LEDs 230 pass through patient tissues to photodetector 232. Light wavelengths not absorbed by the tissues and blood supply are detected by photodetector 232. A current-to-voltage converter 204 receives the current source signal from detector 232 and produces a voltage on signal line 102 that represents the amplitudes of the detected light wavelengths. A signal line 102 is coupled to an input of the gain controlled amplifier 114 and an input of an analog-to-digital converter 226.

The output of analog-to-digital converter 226 may be coupled to a digital filter 224 that may be used to enhance the signal information from the photo-detector 232. A digital-to-analog converter 222 may be coupled to the output of a digital filter 224 so as to convert this output to an analog voltage that may be coupled to an input of gain controlled amplifier 116. According to this specific example embodiment, the photo-detector 232 may have an output that may be coupled directly (or indirectly) to the input of the gain controlled amplifier 114. In addition, the output of the photodetector 232 may be coupled (e.g., indirectly) to the gain controlled amplifier 116 through the digital filter 224. This particular embodiment is directed, in one aspect, to providing a switchover between signal line 102 having the unprocessed information from the photodetector 232 and the signal line 108 having the digitally filtered (enhanced) information from the photodetector 232.

The controller 216, e.g., a digital processor, a microprocessor, a microcontroller, a digital signal processor (DSP), an application specific integrated circuit (ASIC) and/or programmable logic array (PLA), in combination with digital-to-analog converters 218 and 220 may be used for controlling gains of the gain controlled amplifiers 114 and 116. When a selection change, e.g., nurse or doctor initiated, is made between the unfiltered and filtered signal information from the photodetector 232, the gain control signal line 106 may have a control signal from the digital-to-analog converter 220 that is at a maximum voltage at the beginning of a time period T, thereby, according to this embodiment, setting the gain of the gain controlled amplifier 114 to a maximum. As the time period T proceeds, the control signal on the gain control signal line 106 decreases until it is at a minimum, thereby, according to this embodiment, reducing the gain of gain controlled amplifier 114. In a similar, but opposite fashion, the gain control signal line 112 may have a control signal that starts at the beginning of the time period T at a minimum voltage thereby, according to this embodiment, setting the gain of the gain controlled amplifier 116 to a minimum, and as the time period T proceeds, the control signal on the gain control signal line 112 increases until it is at a maximum voltage, thereby, according to this embodiment, increasing the gain of the gain controlled amplifier 116.

Since the outputs of the voltage-to-current converters 122 and 124 may be in parallel, the output current 126 may represent the dominant gain controlled amplifier output signal 118 or 120, e.g., the one having the highest gain and signal input will block the other one. Thus, according to this embodiment, input signals 102 and 108 may be switched without introducing a transient in the output current signal 126. The output current signal 126 may be used to supply sensor information to an oximeter 212, e.g., oximeter display monitor. The timing and clocking circuit 228 may be used for clock signals and timing signals for the light emitting diodes 230 and the controller 216.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A pulse oximetry switching system, the system comprising:
   a pulse oximetry sensor;
   a first gain controlled amplifier having an input coupled to the pulse oximetry sensor;
   a digital filter having an analog input coupled to the pulse oximetry sensor;
   a second gain controlled amplifier having an input coupled to an analog output of the digital filter;
   a first voltage-to-current converter having a voltage input coupled to an output of the first gain controlled amplifier;
   a second voltage-to-current converter having a voltage input coupled to an output of the second gain controlled amplifier, wherein the first and second voltage-to-current converters have outputs coupled together to produce a single current output; and
   a controller having a first gain control output coupled to the first gain controlled amplifier and a second gain control output coupled to the second gain controlled amplifier, the controller adapted to control a gain increase of one of the gain controlled amplifiers over a period of time and a gain decrease of the other gain controlled amplifier over the same period of time, wherein the single current output from the first and second voltage-to-current converters represents the output of the gain controlled amplifier having the highest gain.

2. The apparatus according to claim 1, wherein a current output from the first and second voltage-to-current converters is coupled to an oximeter.

3. The apparatus according to claim 2, wherein the oximeter indicates percent oxygen saturation of blood.

4. The apparatus according to claim 2, wherein the oximeter indicates pulse rate.

5. The apparatus according to claim 3, wherein the pulse oximetry sensor is adapted to attach to a portion of a patient having blood flow therein and wherein the pulse oximetry sensor monitors oxygen saturation of the blood.

6. The apparatus according to claim 1, wherein the pulse oximetry sensor is coupled to the input of the first gain controlled amplifier and the input of the digital filter with a current-to-voltage converter.

7. The apparatus according to claim 1, wherein the pulse oximetry sensor is coupled to the digital filter with an analog-to-digital converter.

8. The apparatus according to claim 1, wherein the analog output of the digital filter is produced with a digital-to-analog converter.

9. The apparatus according to claim 1, wherein the controller comprises at least one of a digital processor, a microprocessor, a microcontroller, a digital signal processor, an application specific integrated circuit, or a programmable logic array, or any combination thereof.

10. The apparatus according to claim 9, wherein the first and second gain control outputs of the microprocessor are produced with first and second digital-to-analog converters, respectively.

11. The apparatus according to claim 1, wherein the current outputs of the first and second voltage-to-current converters are connected in parallel.

12. The apparatus according to claim 1, wherein the controller selects an operational channel for the pulse oximetry sensor by increasing the gain of the gain controlled amplifier associated with that operational channel.

13. A method of manufacturing a pulse oximeter, the method comprising:
   providing a first gain controlled amplifier to which a pulse oximetry sensor may be coupled;
   coupling the pulse oximetry sensor to a digital filter;
   coupling the digital filter to a second gain controlled amplifier;
   coupling the first gain controlled amplifier to a first voltage-to-current converter;
   coupling the second gain controlled amplifier to a second voltage-to-current converter; and
   coupling the first and second voltage-to-current converter outputs together to produce a current output, wherein by providing a controller the gain of one of the gain controlled amplifiers is adapted to increase over a period of time while the gain of the other gain controlled amplifier is adapted to decrease over the same period of time, wherein the current output from the first and second voltage-to-current converters represents the gain controlled amplifier having the highest gain.

14. The method according to claim 13, comprising coupling the current output of the first and second voltage-to-current converters to an oximeter.

15. The method according to claim 14, wherein the oximeter indicates percent oxygen saturation of blood.

16. The method according to claim 14, wherein the oximeter indicates pulse rate.

17. The method according to claim 13, wherein coupling the pulse oximetry sensor to the first gain controlled amplifier and the digital filter is via a current-to-voltage converter.

18. The method according to claim 13, wherein the pulse oximetry sensor is coupled to the digital filter with an analog-to-digital converter.

19. The method according to claim 13, wherein the controller comprises at least one of a digital processor, a microprocessor, a microcontroller, a digital signal processor, an application specific integrated circuit, or a programmable logic array, or any combination thereof.

20. A pulse oximeter channel switching system, the system comprising:
a pulse oximetry sensor;
an unfiltered channel comprising
a first gain controlled amplifier having an input coupled to the pulse oximetry sensor, and
a first voltage-to-current converter having a voltage input coupled to an output of the first gain controlled amplifier;
a filtered channel comprising
a digital filter having an analog input coupled to the pulse oximetry sensor,
a second gain controlled amplifier having an input coupled to an analog output of the digital filter, and
a second voltage-to-current converter having a voltage input coupled to an output of the second gain controlled amplifier;
the first and second voltage-to-current converters having outputs coupled together to produce a single current output; and
a controller having a first gain control output coupled to the first gain controlled amplifier and a second gain control output coupled to the second gain controlled amplifier,
wherein the system is configured so that (i) upon selection of the unfiltered channel, the controller increases the gain of the first gain controlled amplifier over a period of time and deceases the gain of the second gain controlled amplifier over the same period of time so that the single current output from the first and second voltage-to-current converters represents an unfiltered and amplified signal from the pulse oximetry sensor; and
(ii) upon selection of the filtered channel, the controller increases the gain of the second gain controlled amplifier over a period of time and deceases the gain of the first gain controlled amplifier over the same period of time so that the single current output from the first and second voltage-to-current converters represents a filtered and amplified signal from the pulse oximetry sensor.

21. The system according to claim 20, wherein the controller comprises at least one of a digital processor, a microprocessor, a microcontroller, a digital signal processor, an application specific integrated circuit, or a programmable logic array, or any combination thereof.

* * * * *